(12) United States Patent
Reinisch et al.

(10) Patent No.: US 7,622,723 B2
(45) Date of Patent: Nov. 24, 2009

(54) SYSTEM FOR SPORE DETECTION

(75) Inventors: Lou Reinisch, Christchurch (NZ); Sivananthan Sarasanandarajah, Auckland (NZ)

(73) Assignee: Veritide Limited, Christchurch (NZ)

( * ) Notice: Subject to any disclaimer, the term of this patent is extended or adjusted under 35 U.S.C. 154(b) by 0 days.

(21) Appl. No.: 11/470,110

(22) Filed: Sep. 5, 2006

(65) Prior Publication Data
US 2008/0093566 A1  Apr. 24, 2008

Related U.S. Application Data

(60) Provisional application No. 60/719,930, filed on Sep. 23, 2005.

(51) Int. Cl.
*G01N 21/64* (2006.01)
(52) U.S. Cl. .................................. 250/461.2
(58) Field of Classification Search ............. 250/458.1, 250/461.2, 492.1, 339.06; 356/337
See application file for complete search history.

(56) References Cited

U.S. PATENT DOCUMENTS

| | | | | |
|---|---|---|---|---|
| 5,701,012 A | * | 12/1997 | Ho | 250/461.2 |
| 5,863,790 A | * | 1/1999 | Bolea | 435/287.4 |
| 5,895,922 A | * | 4/1999 | Ho | 250/492.1 |
| 5,999,250 A | * | 12/1999 | Hairston et al. | 356/73 |
| 6,498,041 B1 | | 12/2002 | Tabacco et al. | |
| 6,560,478 B1 | | 5/2003 | Alfano et al. | |
| 6,630,299 B2 | * | 10/2003 | Carrion et al. | 435/5 |
| 6,694,799 B2 | * | 2/2004 | Small | 73/24.02 |
| 6,885,440 B2 | * | 4/2005 | Silcott et al. | 356/73 |
| 2003/0108981 A1 | | 6/2003 | Robinson, Jr. | |
| 2005/0073683 A1 | * | 4/2005 | Gard et al. | 356/337 |
| 2005/0094147 A1 | * | 5/2005 | Yaroslavsky et al. | 356/417 |

FOREIGN PATENT DOCUMENTS

| | | |
|---|---|---|
| WO | WO 02/29388 | 4/2002 |
| WO | WO 03/089661 | 10/2003 |
| WO | WO 2004/015421 | 2/2004 |
| WO | WO 2004/048947 | 6/2004 |

OTHER PUBLICATIONS

Bronk et al., "Studies Relating the Fluorescence of CaDPA and DPA to the Fluorescence of Bacillus Spores," AFRL-HE-WP-TR-2005-0055 (May 2005).
Bronk et al., "The Role of DPA in Fluorescence of Bacillus Spores," Proc. 6th Jt. Conf. on Standoff Detection for Chem. and Biol. Defense (Oct. 2004).
U.S. Appl. No. 11/850,181, "Method for Detection or Identification of Bacteria or Bacterial Spores," Lou Reinisch, filed Sep. 5, 2007.

* cited by examiner

*Primary Examiner*—David P Porta
*Assistant Examiner*—Faye Boosalis
(74) *Attorney, Agent, or Firm*—Dann, Dorfman, Herrell and Skillman, P.C.

(57) ABSTRACT

A method for detecting the presence of bacterial spores in a sample comprises non-destructively to the spores carrying out the steps of assessing the fluorescence of the sample, subjecting the sample to UV radiation, and reassessing the fluorescence of the sample to determine the presence of spores. An increase in fluorescence indicates the presence of spores.

47 Claims, 11 Drawing Sheets

Figure 11

SYSTEM FOR SPORE DETECTION

REFERENCE TO PRIOR APPLICATION

This application claims the benefit of U.S. Provisional Application No. 60/719,930, filed Sep. 23, 2005.

FIELD OF THE INVENTION

The present invention relates to a system for the detection of bacterial spores.

BACKGROUND OF THE INVENTION

Systems for the detection of chemical and biological weaponry are of increasing international interest. A biological weapon incorporates an organism (bacteria, virus or other disease-causing organism) or toxin found in nature as a weapon of war. Biological warfare agents of critical concern include bacterial spores such as *Bacillus anthracis* (anthrax), *Clostridium tetani* (tetanus), and *Clostridium Botulinum* (botulism). Particularly *Bacillus* bacteria and *Clostridium* bacteria form bacterial spores.

Dipicolinic acid (pyridine 2,6 dicarboxylic acid) (DPA) is a major component of bacterial spores and it is unique in that it has only been found in spores. Up to 15% of a spore's dry weight may consist of DPA complexed with calcium ions (CaDPA).

U.S. Pat. Nos. 5,701,012 and 5,895,922 disclose a process for detecting the existence of biological particles such as spores whereby fluorescence of the particle is measured and compared against predetermined fluorescence levels.

Bronk et al in Chemical and Biological Sensing (P. J. Gardner, Ed. Proc. SPIE vol 4036 (2000) pp 169-180) disclose observing an increase in fluorescence intensity following heating spores in a water suspension to cause release of DPA by the spores into the water and then exposing the water to UV light.

OBJECT OF THE INVENTION

It is an object of the present invention to provide a system for the detection of bacterial spores which is simpler than the above mentioned processes and/or which at least provides the public with a useful choice.

SUMMARY OF THE INVENTION

In one aspect of the invention there is provided a method for detecting bacterial spores in a sample comprising non-destructively to the spores carrying out the steps of assessing the fluorescence of the sample, subjecting the sample to UV radiation, and reassessing the fluorescence of the sample to detect for the presence of spores.

Preferably the physical state of the sample, such as particulate, liquid, a suspension, or airborne for example, is not altered within the steps of the method.

The method utilises an initial assessment of the fluorescence of the sample followed by irradiation with UV radiation and then a reassessment of the fluorescence of the sample for an increase in the amount of fluorescence between the two assessments. Such fluorescence increase or enhancement is indicative of the presence of spores. The actual fluorescence, or simply a change in fluorescence between the two measurements, may be determined. The fluorescence does not have to be spectrally resolved in order to detect a fluorescence increase but may optionally be spectrally resolved.

In one form of the invention the steps of assessing and reassessing the fluorescence include causing the fluorescence to pass through a filter oriented to pass substantially only horizontally polarised light, and assessing and reassessing the fluorescence by reference to the horizontally polarised fluorescent light. Preferably the excitation light is vertically polarised. Alternatively the excitation light may be unpolarised light.

Optimal wavelengths are generally in the range 200 to 300 nm, more preferably 250 to 300 nm, and optionally about 280 nm for the UV exposure between the assessment and reassessment of fluorescence. The exposure time for optimal enhancement depends upon the intensity of the UV radiation source and the number of spores that may be present in the sample. Preferably the enhancement exposure time is less than 20 minutes, more preferably less than 10 minutes, and most preferably less than 5 minutes.

The sample may be subjected to a pulse of UV radiation, which may be shorter than 10 ns, and the fluorescence is reassessed after a time period, which may be between 0.1-10 ns. Preferably the time period of time corresponds to the fluorescence lifetime of the DPA fluorescence.

The sample may be subjected to a modulated UV signal, and the fluorescence is reassessed for a modulated response. Preferably the reassessment is after a period of time substantially corresponding to the fluorescence lifetime of the DPA fluorescence.

In one embodiment the sample may be immobilised on a support and the step of subjecting the sample to UV radiation occurs by irradiating the sample on the support with UV radiation.

In an alternative embodiment in the sample may be airborne and the step of subjecting the sample to UV radiation occurs by causing the sample to pass through a beam of UV radiation.

In an alternative embodiment the sample may be a solution or a suspension, and the solution or suspension may be irradiated.

In another aspect of the invention there is provided a detector for detecting bacterial spores in a sample comprising a UV source, a detection zone within which the sample may be placed or may pass, means for fluorescence analysis arranged to assess for the presence of spores by reference to an increase in fluorescence following exposure of the sample to a UV source between assessments, without altering the structure of any spore.

The detector is arranged to make an initial measurement of the fluorescence of the sample, followed by irradiation with UV radiation and then a re-measurement of the fluorescence of the sample. The results of the measurements may be output as actual fluorescence measurements, or as a reading of the change in fluorescence between the two measurements.

Preferably the detector is arranged to subject the sample to UV radiation of wavelength in the range 200 to 300 nm, more preferably in the range 250 to 300 nm, and most preferably at about 280 nm.

Preferably the detector is arranged to assess and reassess the fluorescence by reference substantially only to horizontally polarised fluorescent light. Further preferably in this embodiment the excitation light is vertically polarised, but may alternatively be unpolarised. A preferred form of the detector in this embodiment includes a vertically polarising filter to polarise the W radiation from the UV source and a horizontally polarising filter enabling detection of the horizontally polarised fluorescence.

The detector may be arranged to subject the sample to a pulse of UV radiation and to reassess the fluorescence of the sample after a period of time, between 0.1-10 ns, has expired. Preferably the period of time corresponds to the fluorescence lifetime of the DPA fluorescence.

The detector may be arranged to assess the fluorescence of the sample, to subject the sample to a modulated UV signal and to reassess the fluorescence of the sample for a modulated response. Preferably the reassessment is after a period of time substantially corresponding to the fluorescence lifetime of the DPA fluorescence.

In another aspect of the invention there is provided a method of detecting bacterial spores in a sample comprising the steps of providing a detector as described above, positioning the detector so that the sample is in the detection zone, and analysing the spore content of the sample, wherein the step of analysis of the spore content includes measuring the fluorescence of the sample; exposing the sample to UV radiation and then re-measuring the fluorescence of the sample wherein the structure of any spore remains unaltered throughout the steps of the method.

In another aspect of the invention there is provided a method of ascertaining whether a sample, due to its content of bacterial spores, presents a threat to a mammal comprising the steps of providing a detector as described above, setting the sensitivity of the detector at a predetermined threshold above which a threat would be considered to be present, positioning the detector so that the sample is in the detection zone, reading or interpreting the output of the detector as either:

a. above the threshold and thus the sample presents a threat, or
b. below the threshold and thus the sample does not present a threat, wherein the structure of any spore remains unaltered throughout the steps of the method.

Bacterial spores which may be detected by the invention include spores of *Bacillus anthracis, Clostridium tetani,* and *Clostridium botulinum*.

The threat may be of biological warfare. Alternatively the threat may be of bacterial contamination of a material. For example the material may be a foodstuff such as flour or milk powder and bacterial spores may include *Bacillus* spore.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

DEFINITIONS

As used herein the following terms have the meanings given:

"bacterial spore" means an endospore produced within a bacterium.

"fluorescence" means the emission of light of a longer wavelength by a source caused by exposure to light of a shorter wavelength from an external source.

"fluorescence lifetime" refers to how long the fluorescence process exists after the sample is excited.

"sample" means any sample of whatever form including particulate, on a surface or airborne, in solution or suspension including cloudy liquids such as milk.

"support" means some form of substrate, slide or other surface upon which the sample may be immobilised even if only temporarily.

"unaltered" with reference to the spore structure means that the spore is not is not broken down to release the DPA or CaDPA. The DPA and CaDPA remain within the spore structure.

"unaltered" with reference to the physical state of the sample means that the sample is not subjected to any dissolution, suspension, phase change or other process.

"vertically polarised" and "horizontally polarised" in relation to light are used with respect to the scattering plane or surface. In the cases of the samples under investigation, the surface may be the surface of the molecule, or a solid phase; it is relative to the direction of the light and of the species which is responsible for light reflection and/or absorption.

"and/or" means "and" or "or", or both.

As used herein "(s)" following a noun means the plural and/or singular forms of the noun.

The term "comprising" as used in this specification and claims means "consisting at least in part of", that is to say when interpreting independent paragraphs including that term, the features prefaced by that term in each paragraph will need to be present but other features can also be present.

BRIEF DESCRIPTION OF THE DRAWINGS

The invention will now be described by way of example only and with reference to the drawings in which.

DETAILED DESCRIPTION OF THE INVENTION

We have found that DPA and CaDPA in spores will exhibit fluorescence enhancement on UV exposure without first requiring breakdown of the spore structure, by heating in water for example, to release the DPA/CaDPA into the supernatant liquid. The invention comprises non-destructively to the spores:

assessing the fluorescence of a sample (such as but not limited to dust, powder or a solution) which is suspected of containing bacterial spores, exposing the sample to ultraviolet radiation, reassessing the fluorescence of the sample, and determining the presence (or absence) of spores.

Figure 1:
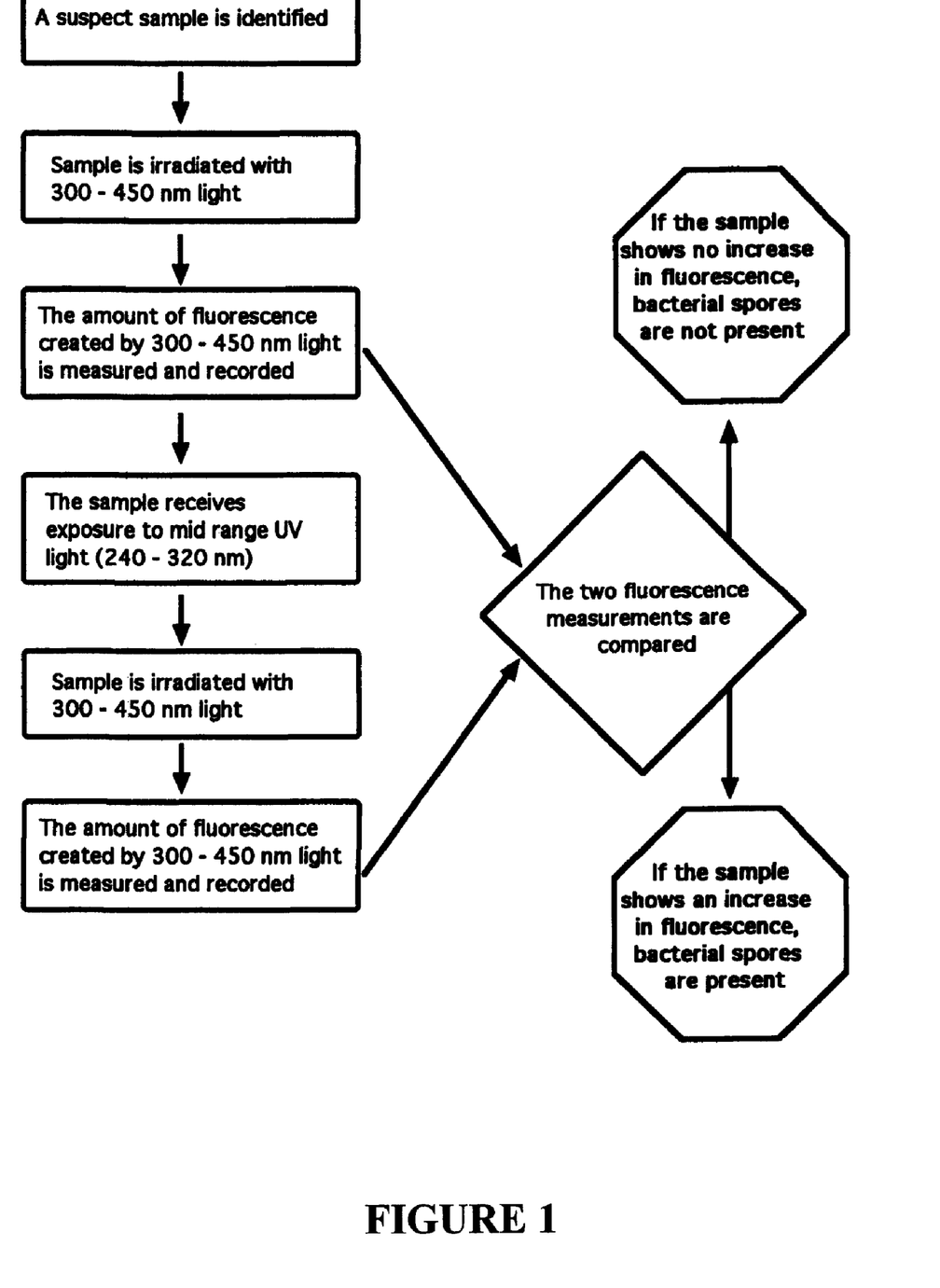
FIG. 1: is a generalised flow diagram of the method of the invention.
Figure 2:
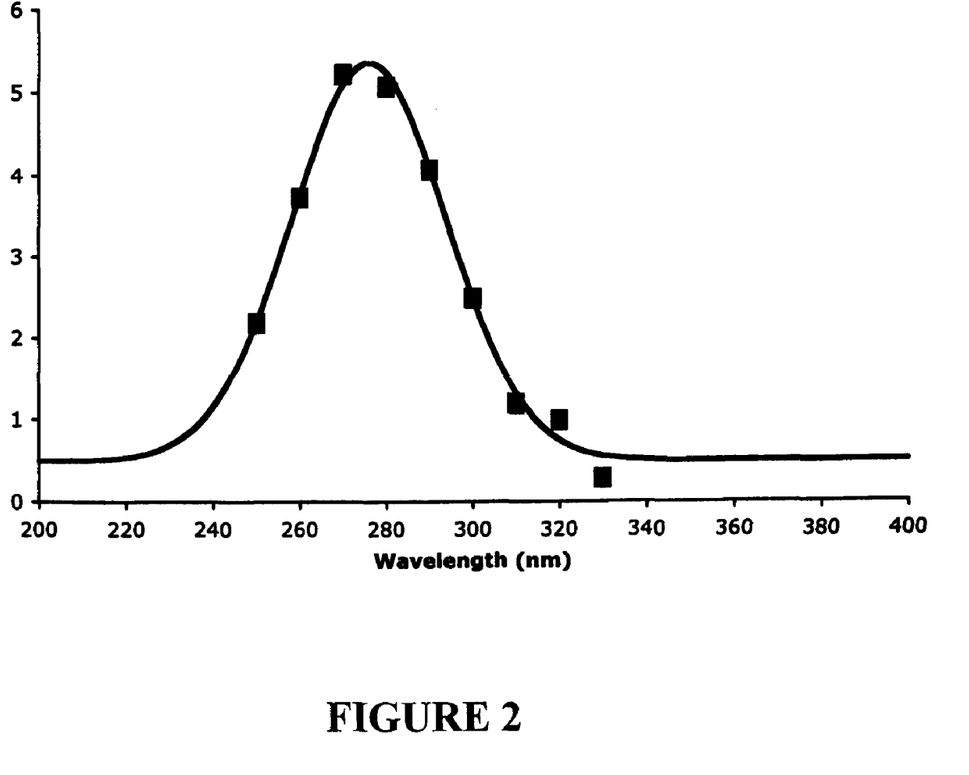
FIG. 2: is a plot of the spectral response for the enhancement of the DPA fluorescence.
Figure 3:
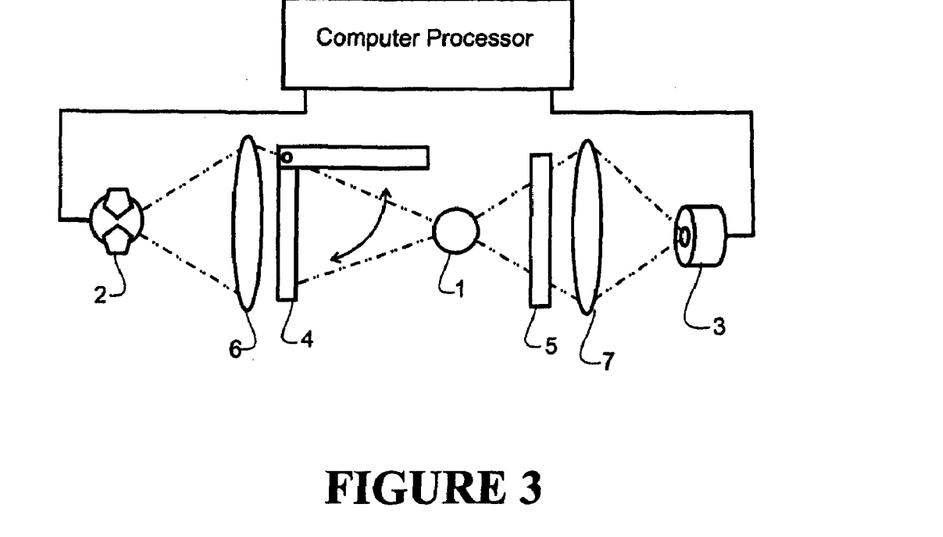
FIG. 3: is a schematic of an embodiment of a detector in accordance with the invention.
Figure 4:
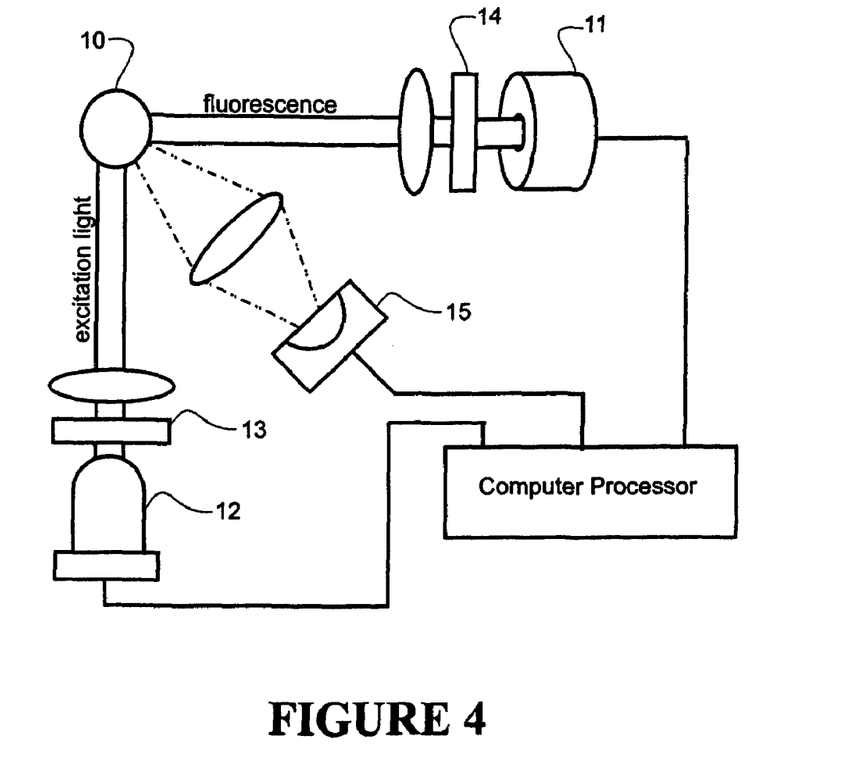
FIG. 4: is a schematic of an alternative embodiment of a detector in accordance with the invention.
Figure 5:
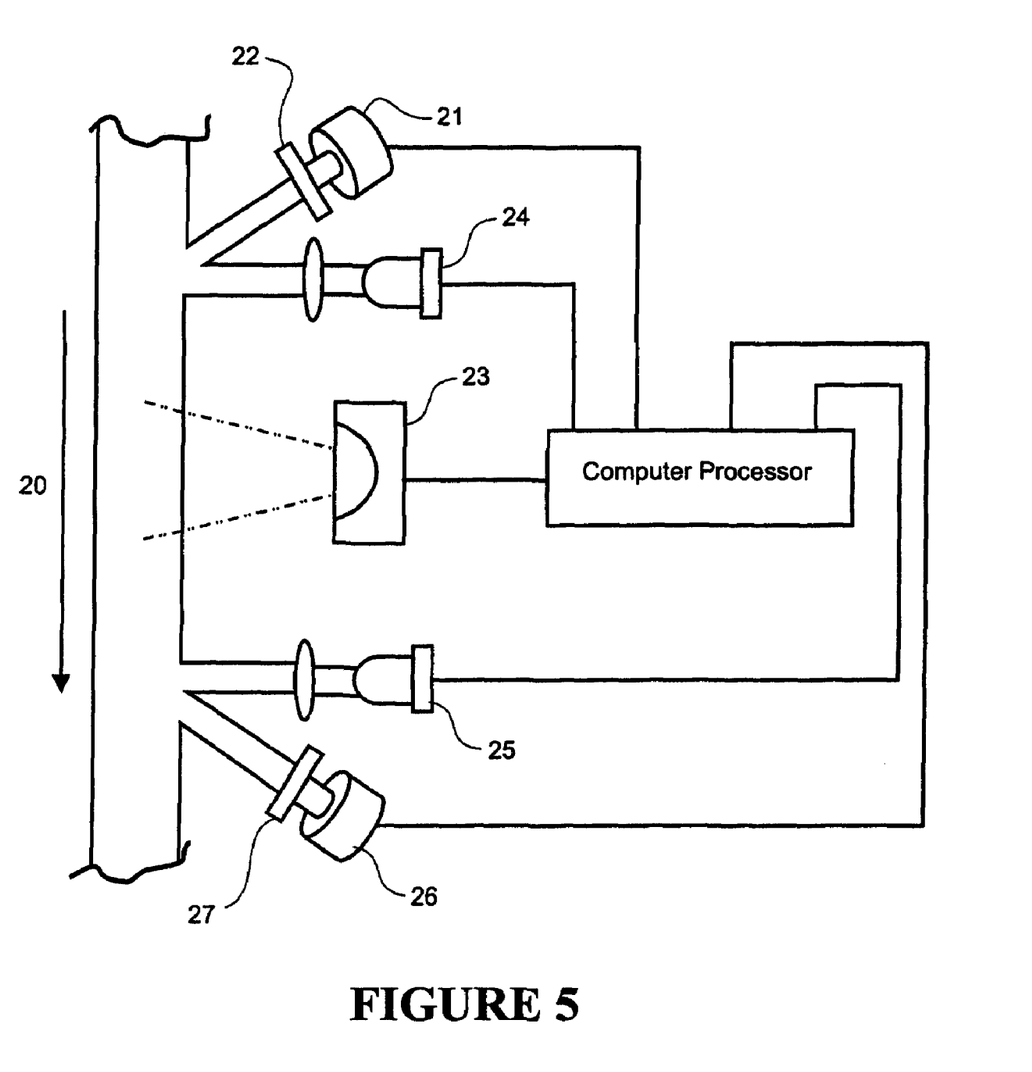
FIG. 5: is a schematic of an alternative embodiment of a detector in accordance with the invention.

If the fluorescence is increased after exposure to UV radiation the sample is assessed as containing bacterial spores. The method is illustrated generally in the flow diagram of FIG. 1 (in which the wavelength ranges are given by way of example).

FIG. 2 shows the spectral response curve for the enhancement of the DPA fluorescence. The full range of enhancement runs from about 230 nm to 330 nm. However the peak enhancement occurs on exposure to UV light of about 280 nm. The squares show measured intensities. The line is a least squares fit of a Gaussian profile to the measured data. As the maximum enhancement is observed at or near 280 nm this is an ideal region of the spectrum for assessing fluorescence enhancement.

In the assessment and reassessment of fluorescence the sample is preferably exposed to UV in the wavelength range 300-400 nm and fluorescence is detected in the wavelength range 300-500 nm.

The invention provides a method for detection of spores which can be carried out non-destructively without requiring heating of spores in a wet environment. Thus the method may be implemented, for example, on a desktop, or an envelope by a handheld detector, via a detector incorporated in a roller in a mail sorting machine, or for airborne spores.

Operational modes may include continuously blowing an air sample through a detector or taking a sample of a suspect powder by picking it up on tape or using an electrostatic screen or taking a sample of a liquid specimen.

FIG. 3 illustrates one embodiment of a detector in accordance with the invention. The Figure illustrates the sample 1, which may be a dry or a wet sample, a broad band UV lamp 2 as the UV source, and a diode detector 3. The UV radiation is focussed onto the sample by means of a lens 6, and the light passes through a long wavelength UV filter 4 (such as a 350 nm filter). The fluorescence passes through a further filter 5 (such as a 450 nm filter) to block the light that is simply reflected from the sample and to make certain that only the fluorescence will be detected before being focused by means of a lens 7, and detected by the detector 3. The amount of light detected for the purposes of this discussion will be called measurement #1. The long wavelength UV filter 4 can then be rotated out of the optical path and the sample is irradiated with all wavelengths of light from the lamp, including the short and mid wavelength UV light. The detector is not used during this time. Finally, the long wavelength UV filter 4 is rotated back into the optical path. The fluorescence passes through filter 5 and lens 7 to detector 3. If the intensity of the fluorescence at detector 3 has increased over measurement #1, then the sample contains bacterial spores. The amount of increase is proportional to the number of spores.

FIG. 4 illustrates a form of a detector and method of the invention that uses no moving parts (like the rotating filter used in FIG. 2). The Figure illustrates the sample 10, which may be a dry or a wet sample, a UV lamp 12, which may be a UV light emitting diode or a diode laser as the UV source, and a diode detector 11. The UV radiation can pass through a long wavelength UV filter 13 (such as a 350 nm filter) if the light from UV source is broadband. If a UV light emitting diode or UV diode laser is used the filter will not be necessary. The light might be further focussed on the sample with a lens. The fluorescence can be collected by a second lens and passes through a filter 14 (such as a 450 nm filter) to block the light that is simply reflected from the sample and to make certain that only the fluorescence will be detected by the detector 11. The amount of light detected for the purposes of this discussion will be called measurement #1. The sample is irradiated with a second UV lamp 15, with 250 to 300 nm UV light. This lamp does not need to be filtered, but can be focussed onto the sample by a lens. The detector 11 is not used during this time. Finally, the sample is again irradiated with the UV lamp 12 and the fluorescence is collected by a lens and passes through the filter 14 (such as a 450 nm filter) to block the light that is simply reflected from the sample and to make certain that only the fluorescence will be detected by the detector 11. If the intensity of the fluorescence at detector 11 has increased over measurement #1, then the sample contains bacterial spores. The amount of increase is proportional to the number of spores.

FIG. 5 illustrates a form of a detector and method of the invention that uses no moving parts but permits one to measure a moving sample, such as milk powder moving on a conveyer belt or envelopes moving through a postal sorter. The Figure illustrates the sample 20, which may be a dry or a wet sample moving at a constant speed as shown by the arrow, a UV lamp 24, which may be a UV light emitting diode or a diode laser as the UV source, and a diode detector 21. The UV radiation can pass through a long wavelength UV filter—not shown (such as a 350 nm filter) if the light from UV source is broadband. If a UV light emitting diode or UV diode laser is a used the filter will not be necessary. The light may be further focussed on the sample with a lens. The fluorescence can be collected by a second lens (not shown) and passes through a filter 22 (such as a 450 nm filter) to block the light that is simply reflected from the sample and to ensure that only the fluorescence will be detected by the detector 21. The amount of light detected for the purposes of this discussion will be called measurement #1. The sample is irradiated by a second UV lamp 23, with 250 to 300 mm UV light. This lamp does not need to be filtered, but can be focussed onto the sample (no lens shown). Finally, the sample is again irradiated with the UV lamp 25, which might be a UV light emitting diode or a diode laser as the UV source, and a diode detector 26. The UV radiation can pass through a long wavelength UV filter—not shown (such as a 350 nm filter) if the light from UV source is broadband. If a UV light emitting diode or UV diode laser is a used the filter will not be necessary. The light might be further focussed on the sample with a lens. The fluorescence can be collected by a second lens (not shown) and passes through a filter 27 (such as a 450 nm filter) to block the light that is simply reflected from the sample and to make certain that only the fluorescence will be detected by the detector 26. If the intensity of the fluorescence at detector 26 has increased over measurement #1, then the sample contains bacterial spores. The amount of increase is proportional to the number of spores. The measurements between detectors 21 and 26 must be delayed by the time required for the sample to move between the two detectors.

UV light sources include lamps (including fluorescent lamps, gas lamps, tungsten filament lamps, quartz lamps, halogen lamps, arc lamps, and pulsed discharge lamps, for example), and UV light emitting diodes, laser diodes, laser of any type capable of producing UV radiation (such as gas, dye or solid state) and two-photon techniques where two separate photons of differing wavelength as used to provide the required excitation wavelength. For example, a 280 nm light necessary to bring about fluorescence enhancement can be achieved from a high intensity of 560 nm light. Two photons of 560 nm could be simultaneously absorbed to create the same effect and response as one 280 nm photon being absorbed. An advantage of such a two-photon absorption is that all optics and the light emitter work in the visible region of the spectrum, whilst the absorption band of the sample is in the UV region. It should be appreciated that when we refer to subjecting the sample to UV radiation, scenarios such as this are included. It is the absorption band which should be considered in this case.

Other than with the two-photon method, the bandwidth of the exciting light does not have to be very narrow. Thus some of the light sources discussed above may not need any filtering, or they could simply be filtered by gratings, interference fitters or coloured glass filters. They could also be filtered by cut-off filters.

The detector may be any photodetectors for the detection of light. These may include, but are not limited to, photodiodes, phototransistors, photoresistors, photomultipliers, pyroelectric detectors, and chemical detectors, such as photographic plates. The detector can be a single element detector like a photodiode that measures all light incident on the detector window, or it could be a image detector, like a silver halide emulsion on a photographic plate or a CCD photodiode array. The detector needs to be sensitive to the range of wavelengths of light emitted from the fluorescing spores.

A detection system of the invention may include means for analysis of the fluorescence. Such means may include computer processing apparatus which, for example records fluorescence recorded or detected before irradiation and compares it with that recorded or detected after, identifies any fluorescence enhancement indicating the presence of spores. The analysis means may determine actual fluorescence measurements or it may simply determine the difference between the first and subsequent recording, and determine if an enhancement has been observed. The analysis means may record and store the outputs or it may simply trigger an alarm for example, if bacterial spores (or spores greater than a threshold limit) are detected.

An alternative form of the invention incorporates the detection of polarised light. The detection of polarised light provides a means to improve the ratio of the fluorescence signal to the background signal.

We have found that if we polarise the irradiating UV light, although the scattered (background) radiation will preserve the polarisation of this light, the fluorescence signal does not. Thus if we irradiate the sample with vertically polarised light, although the scattered light will remain vertically polarised, that light which is fluoresced from the sample (as a result of the presence of the bacterial spores) is a mixture of horizontally polarised and vertically polarised radiation. By measurement of only the horizontally polarised light, fluorescence is measured with little, if any, background scattering. Alternatively the excitation light may be unpolarised light, and only the horizontally polarised fluorescent light is measured.

Figure 6:
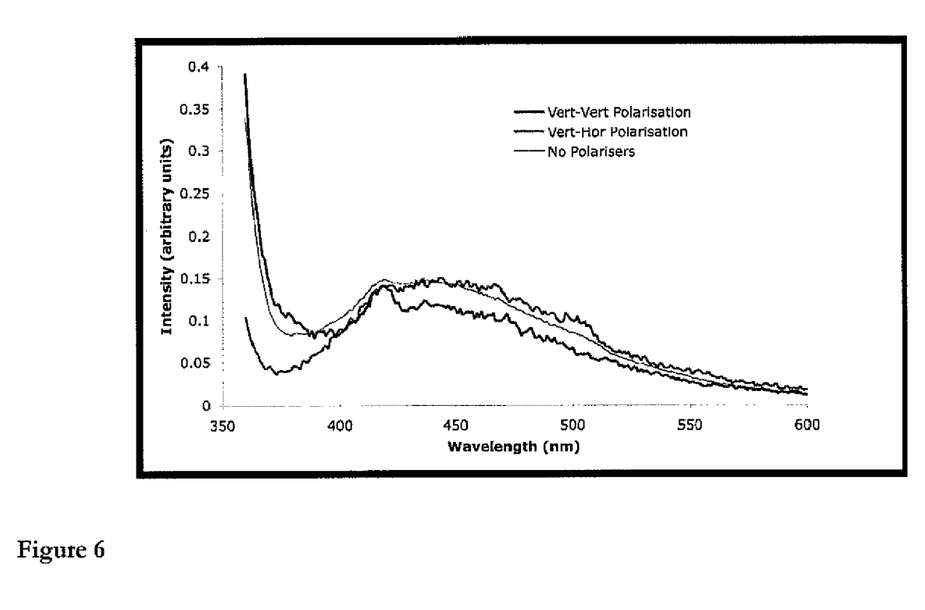
FIG. 6: is plot of fluorescence intensity against emission wavelength showing the effect of using polarised light on the signal to noise ratio.

The terms "vertical" and "horizontal" polarisation are used with reference to the "scattering surface". In the preferred form of this embodiment of the invention we use the 90 degree geometry between incident and scattered light, and the incident radiation is polarised vertically (with respect to the scattering surface or phase). The scattering surface or phase will depend upon the nature of the sample being investigated but is the molecule or species responsible for reflecting and/or absorbing the incident light. FIG. 6 is a plot of intensity against wavelength showing fluorescence from spores observed for the arrangements of no polarisation; vertical-vertical polarisation (ie vertical incoming light; vertical detected fluorescence) and vertical-horizontal ((ie vertical incoming light; horizontal detected fluorescence). This shows an improvement of signal to noise for the vertical-horizontal arrangement as discussed previously. This is particularly true at the lower wavelengths.

Suitable apparatus for this embodiment can be arranged by incorporation of polarising filters into the previously described apparatus. At least a horizontally polarising filter before the detector, and a vertically polarising filter may also be employed with the UV source.

The enhanced fluorescence observed in the methods of all embodiments of the invention is always due to the existence of DPA. However, the wavelengths of fluorescence may be different depending upon the environment of the DPA. Thus in one embodiment of the invention a simple detector may be used to observe only enhancement and thus indicate whether or not spores are present. In an alternative embodiment, using a more specialised detector which resolves the intensity of emission as a function of wavelength, the shape of the fluorescence can be analysed to determine what class of bacterial spores are present in a sample.

Some embodiments of the invention may take advantage of the phenomenon that fluorescence has a distinct lifetime. This lifetime is relative to that of the scattered light, which has a zero lifetime. Specifically, after light is absorbed by the spore it takes a short amount of time for the fluorescence to occur. This is usually between 0.1-10 ns. Thus in general terms if following a short pulsed excitation, emitted light having a zero lifetime is ignored and other emitted light detected, the contribution to the emission by scattering is reduced and thus the signal to noise ratio improved.

An alternative means of taking advantage of this phenomenon involves modulating the intensity of the light, for example in a sinusoidal fashion. The fluorescence of the DPA follows the modulation of the exciting light, delayed by the fluorescence lifetime of the enhanced DPA. Thus in this embodiment a modulated fluorescence signal is detected (again for example a sine wave type signal, if the exciting light was modulated accordingly) delayed by the fluorescence lifetime.

The sensitivity of the detector can be set to ignore the few bacterial spores that occur naturally. Biological weaponry such as anthrax requires approximately 10,000 anthrax spores to lethally infect a person with a 50% probability. Thus the detection limit may be set at for example 100 spores. This is well above the background level for spores, and 1000 times lower than the level needed to lethally infect individuals. Although many bacterial spores are relative harmless to humans, others cause gastrointestinal problems and others like anthrax) are deadly. The levels of bacterial spores should almost always be quite low in the environment thus the detection of bacterial spores above a given threshold level would more than likely signal bioterrorism.

The invention has importance in the bioterrorism field however there are many other applications as would be known to one skilled in the art. Examples include (but are not limited to) the situation in New Zealand where MAF has sprayed certain areas with *Bacillus* bacterial spores as an insecticide against unwanted pests. The method of the invention and a detector of the invention could be employed to detect levels of exposure which would be severely detrimental to the public or such susceptible persons, or to show which regions are safe for such susceptible persons to occupy during spraying.

A further important application of the method and detector of the invention is identifying and quantifying bacterial spores in dried products such as foodstuffs. One particular application is identification and quantification of *Bacillus* bacterial spores in milk powder. Milk powder providers, even with their best precautions, may still have contamination by bacterial spores in their product. Regulatory authorities set guidelines as to what is a minimum spore level for safe use and consumption by the public. Different thresholds will be appropriate for different end uses of the powder. Thus a convenient method of determining whether or not there is a spore presence and what level of presence would be advantageous. The method of the invention is suitable for such an application.

The method of the invention may also be used for detecting spores in a water supply or an air supply, in various medical applications, and in fuels, for example.

The method helps to separate the bacterial spore fluorescence from the fluorescence of other materials for example those found in dust. Thus this enhances discrimination to a point of nearly eliminating false positives.

It is also worthy of note that it may be possible to detect single spores. For example it is common to frequency double, triple and quadruple the light from a Nd:YAG laser. With use of the tripled (355 nm) and the quadrupled (266 nm) light from a Nd:YAG laser, the resolution is such that single spores may be detected by the method of the invention. Lasers other than the Nd:YAG could also be used, such as diode lasers.

The following Experimental Examples illustrate application of the invention to samples in various phases. With reference to the accompanying Figures, it is clear that fluorescence enhancement occurs when spores are present.

EXPERIMENTAL

Example 1

Figure 7:
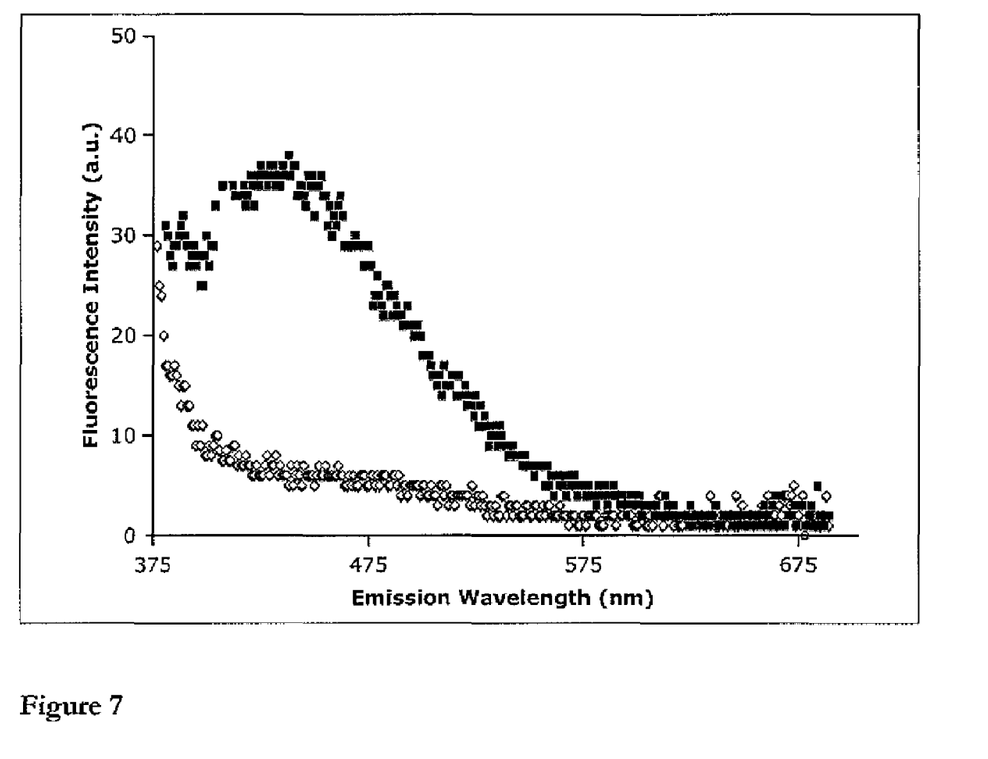
FIG. 7: is a plot of intensity against wavelength of fluorescence before and after irradiation with UV radiation as discussed in Example 1.
Figure 8:
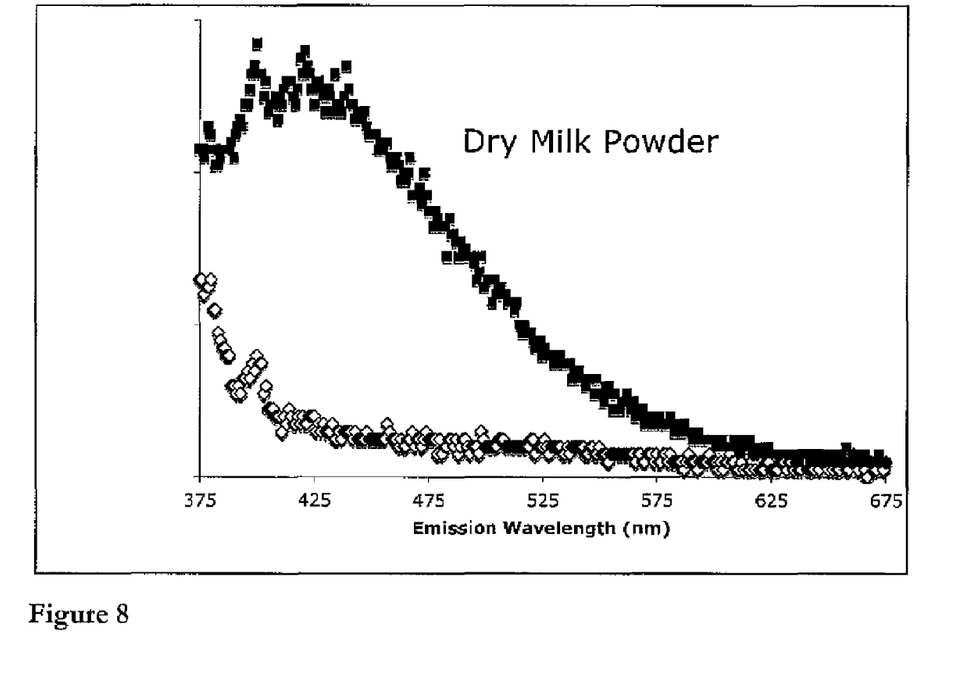
FIG. 8: is a plot of intensity against wavelength of fluorescence before and after irradiation with UV radiation as discussed in Example 2.
Figure 9:
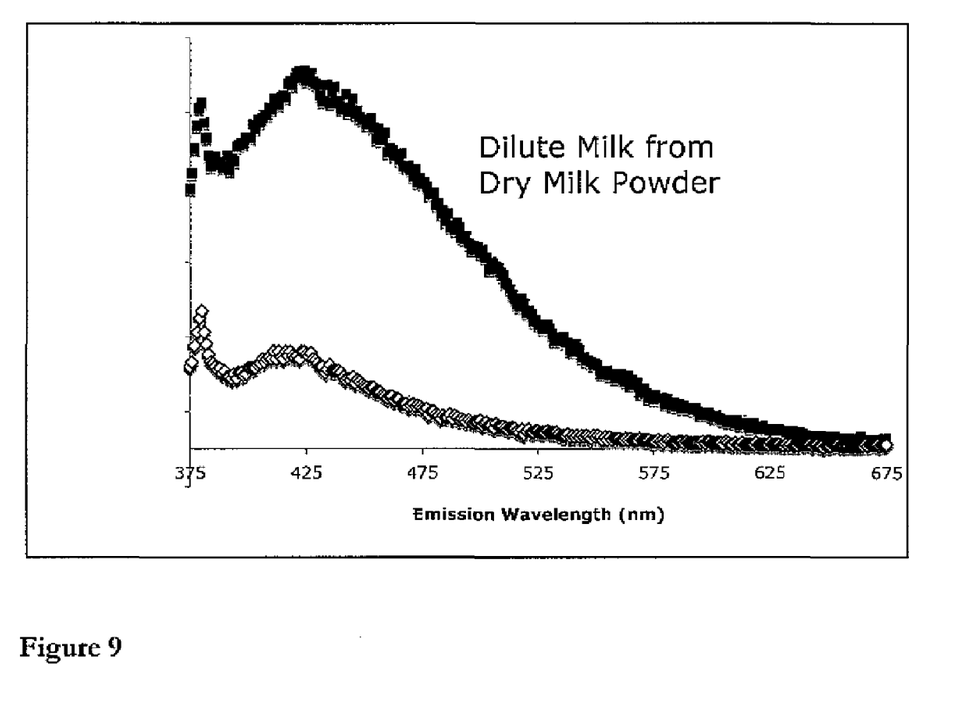
FIG. 9: is a plot of intensity against wavelength of fluorescence before and after irradiation with UV radiation as discussed in Example 3.
Figure 10:
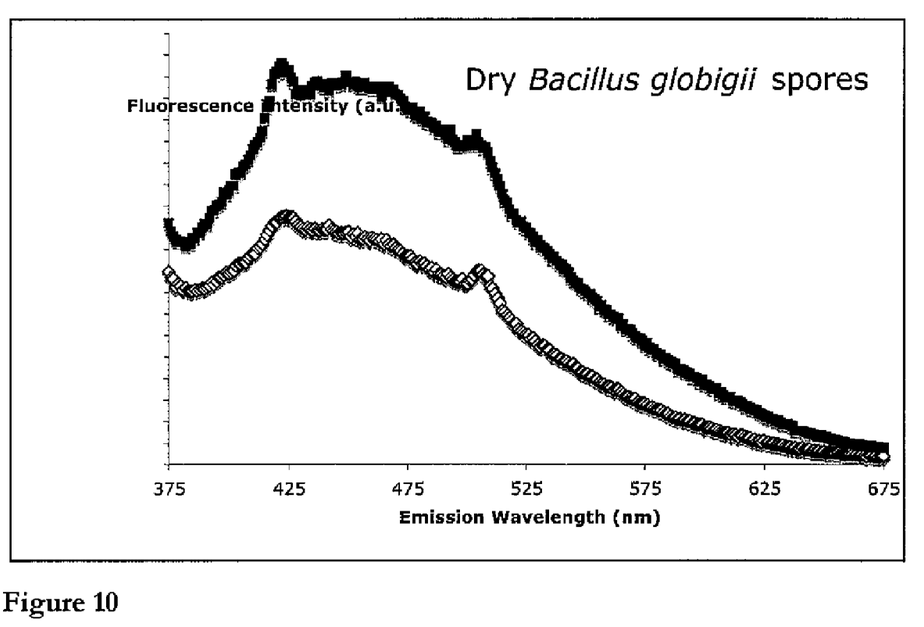
FIG. 10: is a plot of intensity against wavelength of fluorescence before and after irradiation with UV radiation as discussed in Example 4.
Figure 11:
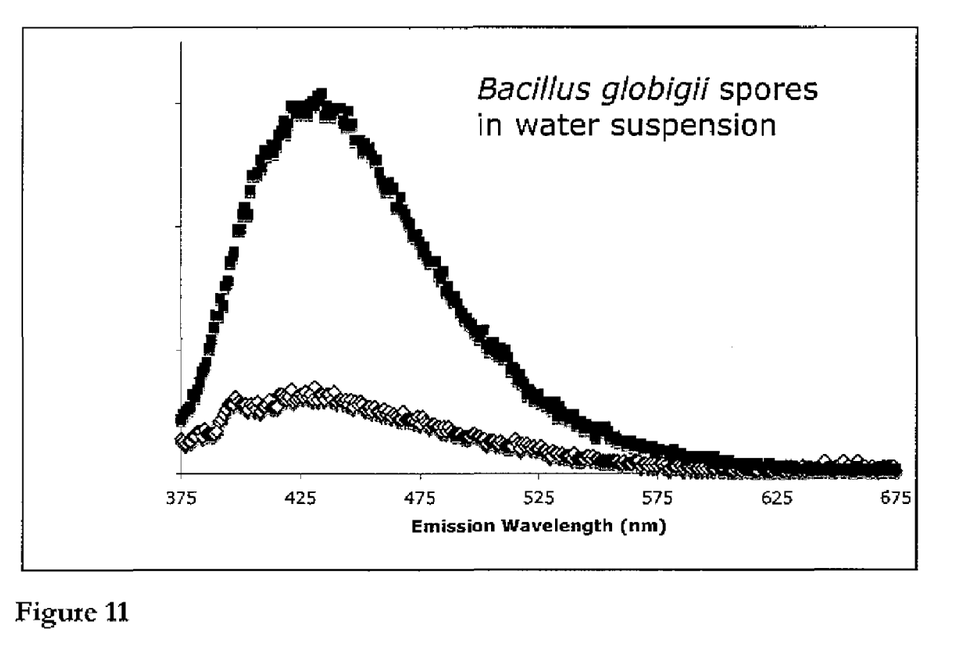
FIG. 11: is a plot of intensity against wavelength of fluorescence before and after irradiation with UV radiation as discussed in Example 5.
Figure 12:
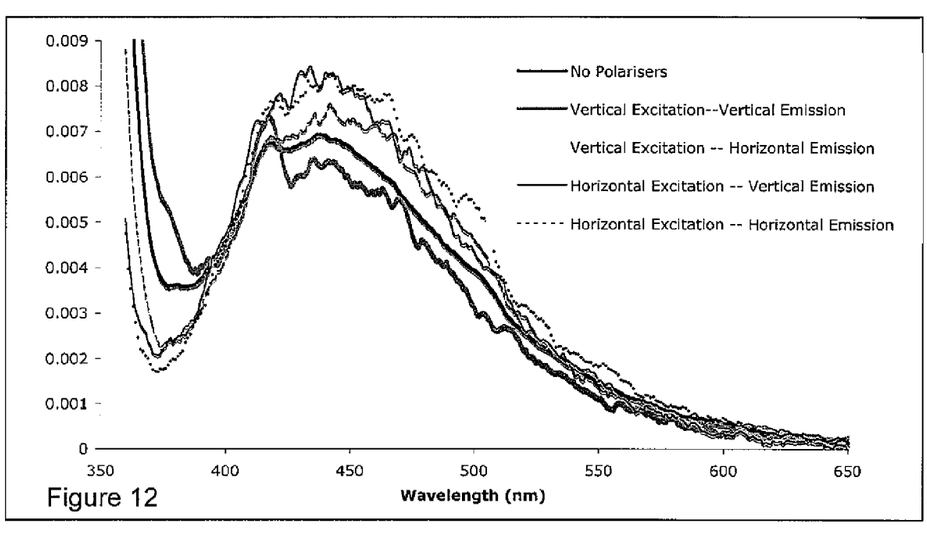
FIG. 12: is a plot of intensity against wavelength of fluorescence before and after irradiation with UV radiation employing polarised light as discussed in Example 6.

FIG. 7 presents the results of an experiment whereby a sample *Bacillus subtilis*, a bacterial spore related to anthrax and commonly used as an anthrax simulant, was irradiated with UV light of wavelength 350 nm. The open diamonds show the fluorescence before irradiation and the solid squares show the fluorescence after being treated with UV light. The enhancement of fluorescence is considerable. The fluorescence is measured and plotted as arbitrary units (a.u.) on the figure. The *B. subtilis* sample was a dilute water suspension of the spores. The suspension measured 0.1 OD at 600 nm in a 1 cm cuvette. The fluorescence was measured using 4 μm bandwidth light at 350 nm and detecting the fluorescence of 375 to 675 nm in 1 nm step with a 4 nm bandwidth. The sample was irradiated with a 150 W xenon arc lamp (unfocussed and 40 cm away from the sample) for 15 minutes.

Example 2

Dry commercial milk powder purchased from a supermarket and used without any additional preparation was studied. With reference to FIG. 8, the fluorescence was measured before (white diamonds) and after (solid squares) irradiation with a 150 W xenon arc lamp (unfocussed and 40 cm away from the sample) for 15 minutes. The fluorescence was measured at 350 nm excitation. The results demonstrate enhanced fluorescence due to the presence of (harmless) spores in the milk powder.

Example 3

The same commercial milk powder as used in Example 2 was dissolved in water to make a dilute sample of milk (the sample measured approximately 1.0 O.D. at 600 nm in a spectrophotometer). With reference to FIG. 9, the fluorescence was measured before (white diamonds) and after (solid squares) irradiation with a 150 W xenon arc lamp (unfocussed and 40 cm away from the sample) for 15 minutes. The fluorescence was measured at 350 nm excitation.

Example 4

A small number of dry *Bacillus globigii* spores (about 10,000) were studied. With reference to FIG. 10 the fluorescence was measured before (white diamonds) and after (solid squares) irradiation with a 150 W xenon arc lamp (unfocussed and 40 cm away from the sample) for 15 minutes. The fluorescence was measured at 350 nm excitation.

Example 5

A dilute suspension of *Bacillus globigii* spores were suspended in water (the sample measured approximately 0.1 OD at 600 nm in a spectrophotometer). With reference to FIG. 11 the fluorescence was measured before (white diamonds) and after (solid squares) irradiation with a 150 W xenon arc lamp (unfocussed and 40 cm away from the sample) for 15 minutes. The fluorescence was measured at 350 nm excitation.

Example 6

A small number of dry *Bacillus globigii* spores (about 10,000) were studied. With reference to FIG. 12 the fluorescence was measured before and after enhancement by UV irradiation, and the lines on the plot indicate the enhancement of fluorescence after irradiation. The sample was enhanced with a 15 W germicidal lamp, unfiltered and 10 cm away from the sample for 15 minutes. The fluorescence was excited with 350 nm UV light. The fluorescence excitation was incident at 45° from the surface containing the spores and the fluorescence was measured at 90° to the incident light. We investigated the fluorescence with unpolarised light incident upon the sample and the unpolarised light emitted from the sample. We also investigated the sample with vertically and horizontally polarized incident light and the vertically and horizontally polarized emitted light. The results are illustrated in FIG. 12. This Figure is a plot of the difference in fluorescence intensity (after minus before enhancement) against wavelength for the different polarization configurations. The total amount of light measured was normalized to account for any intensity fluctuations. It is evident from the Figure that the vertical-horizontal arrangement shows improved signal to noise output.

Where in the foregoing description reference has been made to elements or integers having known equivalents, then such equivalents are included as if they were individually set forth.

Although the invention has been described by way of example and with reference to particular embodiments, it is to be understood that modifications and/or improvements may be made without departing from the scope or spirit of the invention as defined in the accompanying claims.

The invention claimed is:

1. A method of detecting the presence of bacterial spores in a sample comprising non-destructively to the spores carrying out the steps of assessing the sample for fluorescence, subjecting the sample to UV radiation, and reassessing the sample for an increase in fluorescence relative to any fluorescence assessed in said first assessing step, the presence of fluorescence at said assessing step and an increase in fluorescence at said reassessing step being indicative of the presence of spores.

2. A method as claimed in claim 1 wherein the physical state or phase of the sample is not altered within the steps of the method.

3. A method as claimed in claim 2 including measuring actual fluorescence of the sample.

4. A method as claimed in claim 3 including measuring any change in actual fluorescence between the assessment and the reassessment.

5. A method as claimed in claim 1 including subjecting the sample between assessments to UV radiation in the wavelength range 200-300 nm.

6. A method as claimed in claim 1 including subjecting the sample between assessments to UV radiation of about 280 nm wavelength.

7. A method as claimed in claim 6 including causing the fluorescence to pass a filter oriented to pass substantially only horizontally polarised light.

8. A method as claimed in claim 1 comprising assessing and reassessing the fluorescence of the sample by reference to substantially only horizontally polarised fluorescent light.

9. A method as claimed in claim 8 including in the assessment and reassessment exposing the sample to vertically polarised light as the excitation light.

10. A method as claimed in 1 including spectrally resolving the fluorescence observed in the assessment and reassessment steps.

11. A method according to claim 10 including spectrally resolving the fluorescence observed in the assessment or reassessment step or both, and analysing the shape of the fluorescence.

12. A method according to claim 10 including spectrally resolving the fluorescence observed in the assessment or reassessment step or both, and analysing the fluorescence observed at the reassessment step for additional information useful for detecting bacterial spores.

13. A method as claimed in claim 1 including subjecting the sample to UV radiation less than 5 minutes.

14. A method as claimed in claim 1 including assessing the fluorescence of the sample, subjecting the sample to a pulse of UV radiation and reassessing the fluorescence of the sample after a delay.

15. A method as claimed claim 1 including reassessing the fluorescence of the sample after a period of time substantially corresponding to the fluorescence lifetime of DPA.

16. A method as claimed claim 1 including assessing the fluorescence of the sample, subjecting the sample to a modulated UV signal, reassessing the fluorescence of the sample for a modulated response.

17. A method as claimed in claim 1 including reassessing the fluorescence for a modulated response after a period of time substantially corresponding to the fluorescence lifetime of the DPA fluorescence.

18. A method as claimed in claim 1 including assessing and reassessing broadband fluorescence of the sample.

19. A method as claimed in claim 1 including subjecting the sample to UV radiation for a time less than 20 minutes.

20. A method as claimed in claim 1 including subjecting the sample to UV radiation for a time less than 10 minutes.

21. A method as claimed in claim 1 wherein the sample is a solid material immobilised on a support and the method includes subjecting the sample to UV radiation by irradiating the sample on the support with UV radiation and reassessment of the fluorescence of the sample.

22. A method as claimed in claim 1 wherein the sample is airborne and the method includes subjecting the sample to UV radiation by causing the sample to pass through a beam of UV radiation.

23. A method as claimed in claim 1 wherein the sample is a solution or a suspension, and the method includes subjecting the sample to UV radiation by subjecting the solution or suspension to UV radiation.

24. A method of detecting bacterial spores in a sample comprising the steps of providing a detector which comprises a UV source, a detection zone within which a sample may be placed or may pass, means for fluorescence analysis arranged to assess for the presence of spores by reference to an increase in fluorescence following one and then a subsequent exposure of the sample to a UV source without altering the structure of any spore, positioning the detector so that the sample is in the detection zone, analysing the spore content of the sample, wherein the step of analysis of the spore content includes assessing the sample for fluorescence, exposing the sample to UV radiation, and then reassessing the sample for an increase in fluorescence relative to any fluorescence assessed in said first assessing step, the presence of fluorescence at said assessing step and an increase in fluorescence at said reassessing step being indicative of the presence of spores.

25. A method as claimed in claim 24 wherein the physical state or phase of the sample is not altered within the steps of the method.

26. A method as claimed in claim 25 including subjecting the sample to UV radiation between assessments of about 280 nm wavelength.

27. A method as claimed in claim 26 comprising assessing and reassessing the fluorescence of the sample by reference to substantially only horizontally polarised fluorescent light.

28. A method as claimed in claim 27 including in the assessment and reassessment exposing the sample to vertically polarised light as the excitation light.

29. A method of ascertaining whether a sample, due to its content of bacterial spores, presents a threat to a mammal comprising the steps of providing a detector which comprises UV source, a detection zone within which a sample may be placed or may pass, means for fluorescence analysis arranged to assess for the presence of spores by reference to a first assessment of the sample for fluorescence, exposure of the sample to the UV source, and a reassessment of the sample for an increase in fluorescence relative to any fluorescence assessed in said first assessing step, the presence of fluorescence at said first assessment step and an increase in fluorescence at said reassessment step being indicative of the presence of spores, all without altering the structure of any spore; setting the sensitivity of the detector at a predetermined threshold above which a threat would be considered to be present, positioning the detector so that the sample is in the detection zone, and reading or interpreting the output of the detector as either
   a) above the threshold and thus the sample presents a threat, or
   b) below the threshold and thus the sample does not present a threat.

30. A method as claimed in claim 29 wherein the physical state of the sample is not altered within the steps of the method.

31. A method as claimed in claim 29 wherein the mammal is a human.

32. A method as claimed in claim 31 wherein the detector is adapted to detect and identify bacteria used in biological warfare.

33. A method as claimed in claim 32 wherein the detector is adapted to detect bacterial contamination of a foodstuff.

34. A method of detecting the presence of bacterial spores in a sample comprising non-destructively to the spores carrying out the steps of assessing the sample for fluorescence, subjecting the sample to UV radiation, then reassessing the sample for fluorescence, and spectrally resolving fluorescence observed in the assessment and reassessment steps and analysing the fluorescence for an increase in fluorescence indicative of the presence of spores.

35. Apparatus for detecting bacterial spores in a sample comprising:
   a source or sources of UV radiation disposed for irradiating a sample and operable to irradiate the sample with UV radiation having a wavelength effective to cause fluorescence of the sample and subsequently with UV radiation having a wavelength effective to cause a photochemical change in the sample;
   a radiation detector disposed for receiving fluorescence radiation from the sample when irradiated by said source or sources of UV radiation and generating a fluorescence signal upon receiving said fluorescence radiation; and
   a computer apparatus operatively connected to said radiation detector or detectors and programmed to (a) record a first fluorescence signal from said radiation detector after the sample is first irradiated with UV radiation having a wavelength effective to cause fluorescence of the sample; (b) record a second fluorescence signal from said radiation detector after the sample is irradiated with UV radiation having a wavelength effective to cause a photochemical change in the sample and then re-irradiated with UV radiation having a wavelength effective to cause fluorescence of the sample; (c) compare said first and second fluorescence signals; and then (d) determine if there is any enhancement of the fluorescence of the sample to thereby detect the presence of bacterial spores in the sample non- destructively to the spores.

36. An apparatus as claimed in claim 35 wherein said source or sources of UV radiation comprise(s) first and second sources of UV radiation wherein the first source is operable to irradiate the sample with UV radiation having the wavelength effective to cause fluorescence of the sample and the second source is operable to irradiate the sample with UV radiation having the wavelength effective to cause a photochemical change in the sample, and
   said radiation detector comprises first and second radiation detectors wherein the first radiation detector is disposed for receiving the fluorescence radiation from the sample when irradiated by the first source UV radiation and generating the first fluorescence signal upon receiving said fluorescence radiation and the second radiation detector is disposed for receiving fluorescence radiation from the sample when re-irradiated by the second source of UV radiation and generating the second fluorescence signal upon receiving said fluorescence radiation.

37. A detector as claimed in claim 36 wherein said source or sources of UV radiation is or are operable to irradiate the sample with UV radiation having a wavelength in the range of 200-300 nm as the radiation having the wavelength effective to cause fluorescence of the sample.

38. A detector as claimed in claim 37 wherein said source or sources of UV radiation is or are operable to irradiate the sample with UV radiation having a wavelength of about 280 nm wavelength as the radiation having the wavelength effective to cause fluorescence of the sample.

39. A detector as claimed in claim 35 wherein said radiation detector is arranged to detect substantially only horizontally polarized fluorescent radiation.

40. A detector as claimed in claim 39 wherein said source or sources of UV radiation include a source of UV radiation operable to irradiate the sample with vertically polarized UV radiation as the radiation having the wavelength effective to cause fluorescence of the sample.

41. A detector as claimed in claim 35 wherein said source or sources of UV radiation include a source of UV radiation operable to irradiate the sample with vertically polarized UV radiation as the radiation having the wavelength effective to cause fluorescence of the sample.

42. A detector as claimed in claim 35 wherein said computer apparatus is arranged to spectrally resolve the first and second florescence signals.

43. A detector according to claim 35 wherein said computer apparatus is arranged to spectrally resolve the first and second fluorescence signals and analyse the shape of the fluorescence signals.

44. A detector according to claim 35 wherein said computer apparatus is arranged to spectrally resolve the second fluorescence signal, and analyse the spectrally resolved second fluorescence signal for additional information useful for detecting bacterial spores.

45. A detector as claimed in claim 35 wherein said source or sources of UV radiation include a source of UV radiation operable to irradiate the sample with UV radiation having a wavelength effective to cause a photochemical change in the sample as a pulse of said UV radiation, and wherein said computer apparatus is arranged to record said second fluorescence signal after a time period from the end of said pulse of between 0.1-10 ns.

46. A detector as claimed in claim 45 wherein said computer apparatus is arranged to record said second fluorescence signal after a time period corresponding to a lifetime of the fluorescence.

47. A detector as claimed in claim 35 wherein said source or sources of UV radiation is or are operable to irradiate the sample with modulated UV radiation, and said radiation detector is arranged to detect a modulated fluorescence response.

* * * * *